(12) United States Patent
Wang et al.

(10) Patent No.: US 12,298,542 B2
(45) Date of Patent: May 13, 2025

(54) OPTICAL PROBE

(71) Applicant: Industrial Technology Research Institute, Hsinchu (TW)

(72) Inventors: Chy-Lin Wang, Hsinchu County (TW); Chi-Shen Chang, Hsinchu County (TW); Yuan-Chin Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 707 days.

(21) Appl. No.: 17/555,509

(22) Filed: Dec. 20, 2021

(65) Prior Publication Data

US 2023/0127319 A1 Apr. 27, 2023

(30) Foreign Application Priority Data

Oct. 21, 2021 (TW) ................................. 110139150

(51) Int. Cl.
*G02B 5/18* (2006.01)
*G02B 3/06* (2006.01)

(52) U.S. Cl.
CPC ............. *G02B 5/1814* (2013.01); *G02B 3/06* (2013.01); *G02B 5/1871* (2013.01)

(58) Field of Classification Search
CPC ...... G02B 5/1814; G02B 5/1871; G02B 5/18; G02B 3/06; G02B 3/08; G02B 3/02;
(Continued)

(56) References Cited

U.S. PATENT DOCUMENTS 5,442,480 A * 8/1995 Swanson ............ G02B 27/4211
359/356
5,742,431 A * 4/1998 Meyers ............... G02B 17/0808
359/566
(Continued)

FOREIGN PATENT DOCUMENTS

IN 110430816 11/2019
TW I251684 3/2006
(Continued)

OTHER PUBLICATIONS

Junyoung Kim et al., "Flexible endoscopic micro-optical coherence tomography for three-dimensional imaging of the arterial microstructure", Scientific Reports, Jun. 8, 2020, pp. 1-11.
(Continued)

*Primary Examiner* — Jyotsna V Dabbi
(74) *Attorney, Agent, or Firm* — JCIPRNET (57) ABSTRACT

An optical probe includes a cylindrical lens adapted to receive and transmit incident light. A light-emitting surface of the cylindrical lens is a curved end surface having a concentric ring-shaped diffractive microstructure. A working position of the optical probe is a position where a diffraction order is 1 when the incident light having a design wavelength between a first wavelength and a second wavelength passes through the diffractive microstructure. When passing through the cylindrical lens, the incident light having the first wavelength produces a diffraction effect with the diffractive microstructure and is converged at a first wavelength working position approximately the same as the working position of the optical probe with the diffraction order of 1. After being refracted by the curved end surface, the incident light having the second wavelength is converged at a second wavelength working position approximately the same as the working position of the optical probe.

18 Claims, 9 Drawing Sheets

(58) Field of Classification Search
CPC ........ G02B 6/262; G02B 23/00; G02B 23/02; G02B 23/24; G02B 23/2469; G02B 23/26; G02B 27/0955; G02B 27/0966; G02B 27/44; G02B 27/42; G02B 27/4205; G02B 27/4211; G02B 27/4227; G02B 27/0944; G02B 27/1086; G02B 26/106; G02B 26/0808; G02B 26/123; G02B 26/0816; G02B 5/1876; G02B 5/04; G02B 6/02061; G02B 17/08; G02B 21/04; G02B 23/2423; G02B 27/0037; A61B 1/00096; A61B 1/07; A61B 1/0638; A61B 5/0084; A61B 5/0066; A61B 5/0073; A61B 2090/3614; A61B 1/041; A61B 3/102; A61B 5/0075; A61B 2562/0233; G02F 1/0102; G02F 2201/02; G01J 3/18; G01J 3/1852; G01J 3/1861

USPC .......................................................... 359/558

See application file for complete search history.

(56) References Cited

U.S. PATENT DOCUMENTS

| | | | |
|---|---|---|---|
| 8,760,663 | B2 | 6/2014 | Tearney et al. |
| 8,792,170 | B2 * | 7/2014 | Boubis ............... G02B 27/4277 359/356 |
| 10,646,105 | B2 | 5/2020 | Li et al. |
| 10,682,044 | B2 | 6/2020 | Wu et al. |
| 2006/0109478 | A1 | 5/2006 | Tearney et al. |
| 2010/0174145 | A1 * | 7/2010 | Lee ..................... A61B 5/0066 600/182 |
| 2013/0242053 | A1 | 9/2013 | Bjelkhagen et al. |
| 2018/0256032 | A1 | 9/2018 | Takeuchi et al. |
| 2020/0033584 | A1 | 1/2020 | Jeong et al. |
| 2020/0249377 | A1 * | 8/2020 | Niwa .................. G02B 5/1852 |

FOREIGN PATENT DOCUMENTS

| | | |
|---|---|---|
| TW | 200944776 | 11/2009 |
| TW | 201022837 | 6/2010 |
| TW | I326078 | 6/2010 |
| TW | 201102636 | 1/2011 |
| TW | 201800049 | 1/2018 |
| TW | 108700460 | 10/2018 |
| TW | 202134628 | 9/2021 |
| WO | 2007084903 | 7/2007 |

OTHER PUBLICATIONS

Alexandre R. Tumlinson et al., "In vivo ultrahigh-resolution optical coherence tomography of mouse colon with an achromatized endoscope", Journal of Biomedical Optics, Dec. 2006, pp. 1-8.

Wu Yuan et al., "Super-achromatic monolithic microprobe for ultrahigh-resolution endoscopic optical coherence tomography at 800 nm", Nature Communications, Nov. 16, 2017, pp. 1-9.

Jiefeng Xi et al., "Diffractive catheter for ultrahigh-resolution spectral-domain volumetric OCT imaging", Optics Letters, Apr. 1, 2014, pp. 2016-2019.

Jessica Mavadia-Shukla et al., "High-speed, ultrahigh-resolution distal scanning OCT endoscopy at 800 nm for in vivo imaging of colon tumorigenesis on murine models", Biomed Opt Express, Aug. 1, 2018, pp. 3731-3739.

Hyeon-Cheol Park et al., "Broadband rotary joint for high-speed ultrahigh-resolution endoscopic OCT imaging at 800 nm", Optics Letters, Dec. 1, 2017, pp. 4978-4981.

Hui-Hsiung Lin, "Diffractive / Refractive Hybrid Lens Applied to Optical System Design", Instruments Today, with English abstract, Jun. 1, 2004, pp. 49-63.

Chia-Pin Liang et al., "A forward-imaging needle-type OCT probe for image guided stereotactic procedures", Optics Express, Dec. 8, 2011, pp. 26283-26294.

Woonggyu Jung et al., "Numerical analysis of gradient index lens-based optical coherence tomography imaging probes", Journal of Biomedical Optics, Dec. 30, 2010, pp. 1-11.

M Samir Jafri et al., "Optical coherence tomography in the diagnosis and treatment of neurological disorders", Journal of Biomedical Optics, Oct. 31, 2005, pp. 1-11.

"Office Action of Taiwan Counterpart Application", issued on Sep. 5, 2022, p. 1-p. 10.

* cited by examiner

OPTICAL PROBE

CROSS-REFERENCE TO RELATED APPLICATION

This application claims the priority benefit of Taiwanese application no. 110139150, filed on Oct. 21, 2021. The entirety of the above-mentioned patent application is hereby incorporated by reference herein and made a part of this specification.

BACKGROUND

Technical Field

The disclosure relates to an optical probe.

Description of Related Art

At present, commercially available optical coherent tomography probes have three commonly used light source wavelengths: 880/1310/1550 nm. Since the optical coherent tomography probe may produce different chromatic dispersions for incident light of different wavelengths, change of the wavelength of the incident light of the optical coherent tomography probe may change a position of a converging point, resulting in a change of a working distance.

However, regarding an optical coherent tomography application, if it is unable to meet the requirement that the change of the working distance be less than 10 μm upon change of the wavelength of the incident light, the probe is required to be changed if tomographic images of different wavelengths are to be observed. To change the probes corresponding to different wavelengths requires re-calibration of an optical path of a reference arm. In addition, due to a color difference produced by different wavelengths, a probe detection position may be deviated, i.e., detection positions of different wavelengths are different. Therefore, to change the probe during an operation may prolong the process and increase the risk in the operation. Therefore, a single optical coherent tomography probe covering a relatively large wavelength range is needed to effectively improve accuracy of an implantation position of a stimulation electrode.

SUMMARY

One of the exemplary embodiments of the disclosure is directed to an optical probe including a cylindrical lens adapted to receive and transmit an incident light, a light-emitting surface of the cylindrical lens is a curved end surface, and the curved end surface has a concentric ring-shaped diffractive microstructure, wherein a working position of the optical probe is a position where a diffraction order is 1 when the incident light having a design wavelength passes through the diffractive microstructure. When the incident light having a first wavelength passes through the cylindrical lens, the incident light produces a diffraction effect with the diffractive microstructure and is converged at a first wavelength working position with the diffraction order of 1, and the first wavelength working position and the working position of the optical probe are approximately the same. After the incident light having a second wavelength is refracted by the curved end surface of the cylindrical lens, the incident light with the second wavelength is converged at a second wavelength working position, and the second wavelength working position is approximately the same as the working position of the optical probe. The design wavelength is between the first wavelength and the second wavelength.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Reference will now be made in detail to the embodiments of the disclosure, examples of which are illustrated in the accompanying drawings, but the provided examples are not intended to limit a scope of the disclosure. Moreover, the component sizes in the drawings are drawn for convenience of explanation, and do not represent actual component size ratios. To facilitate understanding, similar components will be described with the same symbols in the following description.

In the description of the embodiments of the disclosure, different examples may use repeated reference symbols and/or words. These repeated symbols or words are used for the purpose of simplification and clarity, and are not used to limit a relationship between various embodiments and/or appearance structures. Moreover, in the following disclosed content of the specification, if a first feature is described to be formed on or above a second feature, it means that it includes an embodiment in which the formed first feature is in direct contact with the second feature, and also includes an embodiment in which an additional feature is formed between the aforementioned first feature and the aforementioned second feature, and the aforementioned first feature and the aforementioned second feature may not be in direct contact.

Figure 1A:
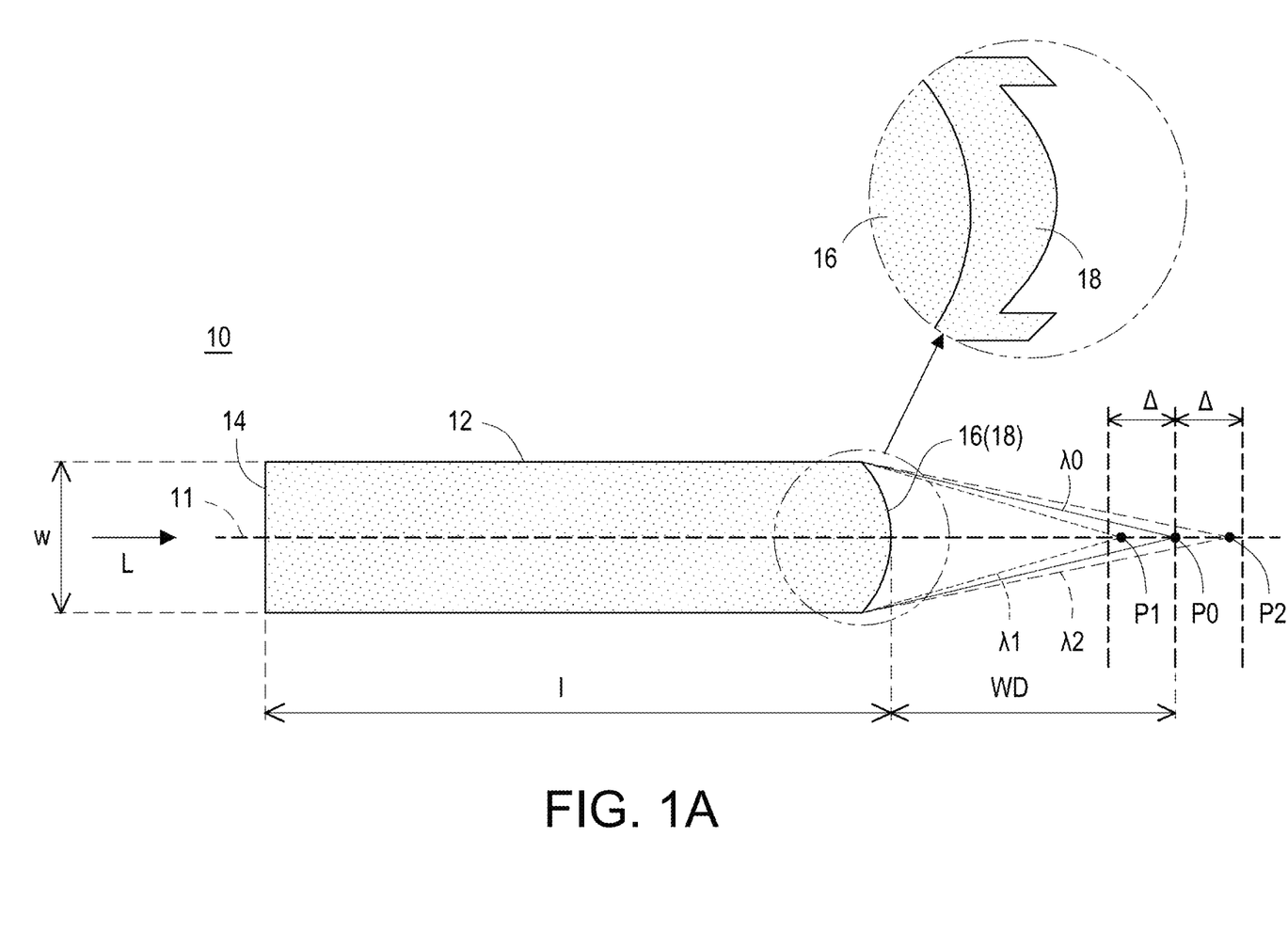
FIG. 1A is a schematic diagram of an optical probe according to an embodiment of the disclosure.

FIG. 1A is a cross-sectional view of an optical probe 10. The optical probe 10 includes a cylindrical lens 12. The cylindrical lens 12 is a cylindrical object that may partially transmit light and has a uniform refractive index. In an embodiment, a length 1 of the cylindrical lens 12 is about 5 mm to 10 mm, and a width w (i.e., a diameter of the cylindrical lens 12) is about 250 μm to 880 μm. In an embodiment, a material of the cylindrical lens 12 may be a polymer compound, plastic, glass, etc. In an embodiment, the refractive index of the cylindrical lens is about 1.5 to 1.8.

The cylindrical lens 12 is adapted to receive and transmit incident light L, and has a flat end surface 14 and a curved end surface 16 opposite to each other. The flat end surface 14 is a light incident surface of the cylindrical lens 12 and is coupled to an optical fiber (not shown), so that the incident light L having different wavelengths $\lambda 0$, $\lambda 1$, and $\lambda 2$ is guided into the cylindrical lens 12 by the optical fiber. The curved end surface 16 is opposite to the flat end surface 14 and is a light-emitting surface of the cylindrical lens 12. In an embodiment, the curved end surface 16 is a spherical surface. In another embodiment, the curved end surface 16 is an aspherical surface.

The curved end surface 16 of the cylindrical lens 12 has diffractive microstructure 18 with a concentric ring-shaped centered on a first optical axis 11 of the cylindrical lens 12. In an embodiment, the diffractive microstructure 18 and the curved end surface 16 of the cylindrical lens 12 are formed integrally. In another embodiment, the diffractive microstructure 18 may be formed independently, and then the diffractive microstructure 18 is attached to the curved end surface 16 of the cylindrical lens 12, which is not limited by the disclosure.

The diffractive microstructure 18 is designed at a design wavelength $\lambda 0$, so that when a wavelength of the incident light L is equal to the design wavelength $\lambda 0$, good diffraction efficiency is achieved. A working position P0 of the optical probe 10 is defined as a position where a diffraction order m=1 when the incident light L of the design wavelength $\lambda 0$ passes through the diffractive microstructure 18, and a working distance WD of the optical probe 10 is defined as a distance between the working position P0 of the design wavelength $\lambda 0$ and the curved end surface 16. When the wavelength of the incident light L is the first wavelength $\lambda 1$ that is different from the design wavelength $\lambda 0$, the incident light L is subjected to a diffraction effect and converged at a position P1 where the diffraction order m=1, and the position P1 is referred to as a first wavelength working position. When the wavelength of the incident light L is a second wavelength $\lambda 2$ different from the design wavelength $\lambda 0$, it is refracted by the curved end surface 16 and converged at a second wavelength working position P2. Distances between the first wavelength working position P1 and the second wavelength working position P2 relative to the curved end surface 16 are referred to as a first wavelength working distance and a second wavelength working distance. The design wavelength $\lambda 0$ is between the first wavelength $\lambda 1$ and the second wavelength $\lambda 2$, and the first wavelength working position P1 and the second wavelength working position P2 are approximately the same as the working position P0 of the design wavelength $\lambda 0$. The so-called "approximately the same" refers to that the first wavelength working position P1 and the second wavelength working position P2 may have some deviations from the working position P0 of the design wavelength $\lambda 0$, but since an amount of such deviation is very small, when the optical probe 10 uses the incident light L with different wavelengths, a working effect thereof is not affected. In detail, as shown in FIG. 1A, the deviations of the first wavelength working position P1 and the second wavelength working position P2 relative to the working position P0 of the design wavelength $\lambda 0$ are all less than a distance Δ. In an embodiment, the distance Δ is less than 10 μm, which meets a working requirement of an optical coherent tomography probe, so that when observing tomographic images of different wavelengths, the optical probe does not need to be replaced.

Figure 1B:
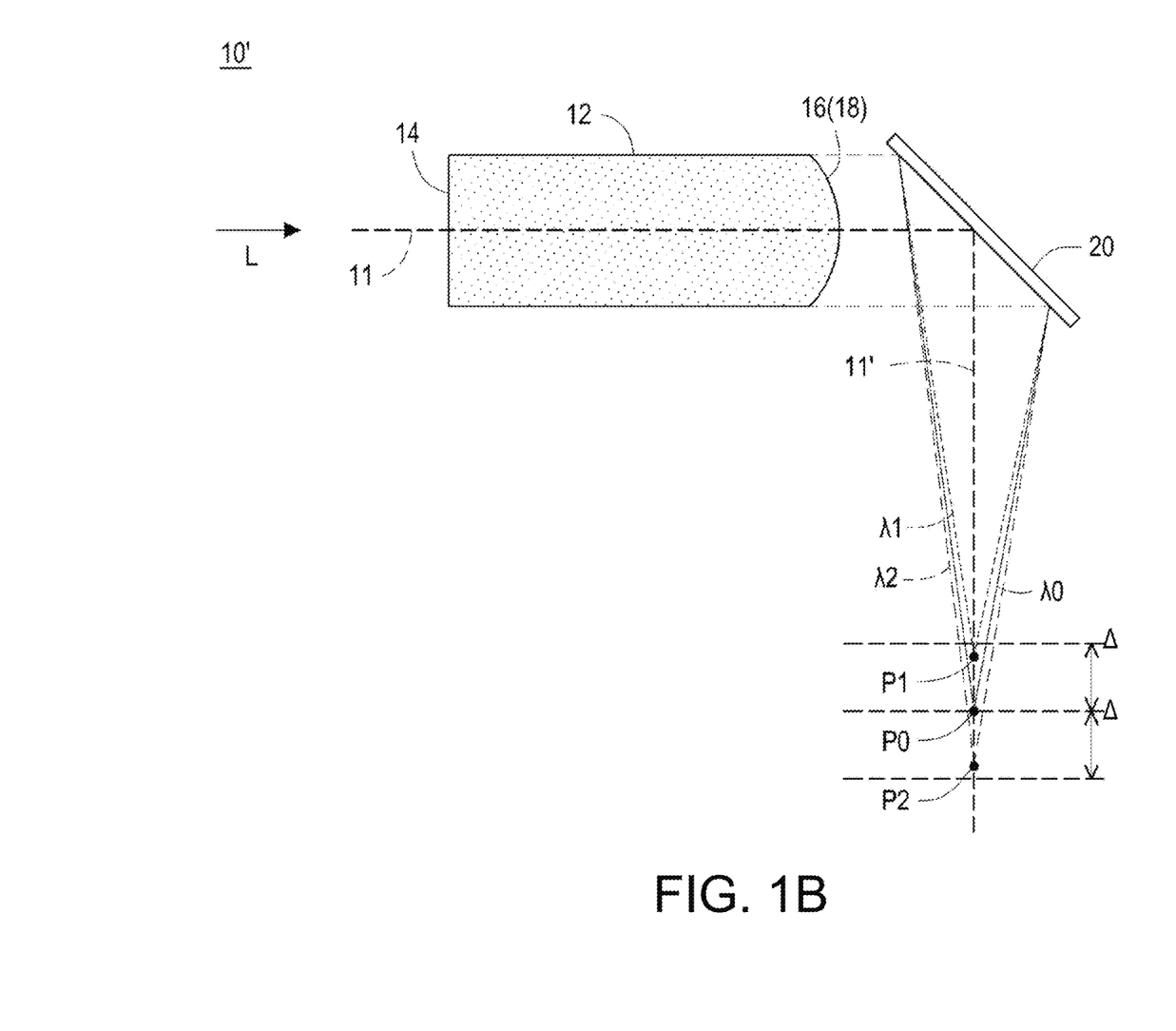
FIG. 1B is a schematic diagram of an optical probe according to another embodiment of the disclosure.

FIG. 1B is a cross-sectional view of an optical probe 10' according to another embodiment. The optical probe 10' is similar to the optical probe 10 of FIG. 1A, but it should be noted that the optical probe 10' further includes a reflector 20, which is disposed behind the curved end surface 16 of the cylindrical lens 12, so that the incident light L is reflected and turned by the reflector 20 after leaving the cylindrical lens 12, and move forward along a second optical axis 11', wherein the second optical axis 11' and the first optical axis 11 of the cylindrical lens 12 are perpendicular to each other.

When the incident light L with different wavelengths $\lambda 0$, $\lambda 1$, and $\lambda 2$ is incident along the first optical axis 11 of the cylindrical lens 12, it is reflected by the reflector 20 and converged at the working positions P0, P1, and P2. Through the reflector 20, the incident light L passing through the cylindrical lens 12 of the optical probe 10' may be deflected by 90 degrees with respect to the first optical axis 11 of the cylindrical lens 12, so as to facilitate detections in different directions in use and increase operational flexibility.

Figure 1C:
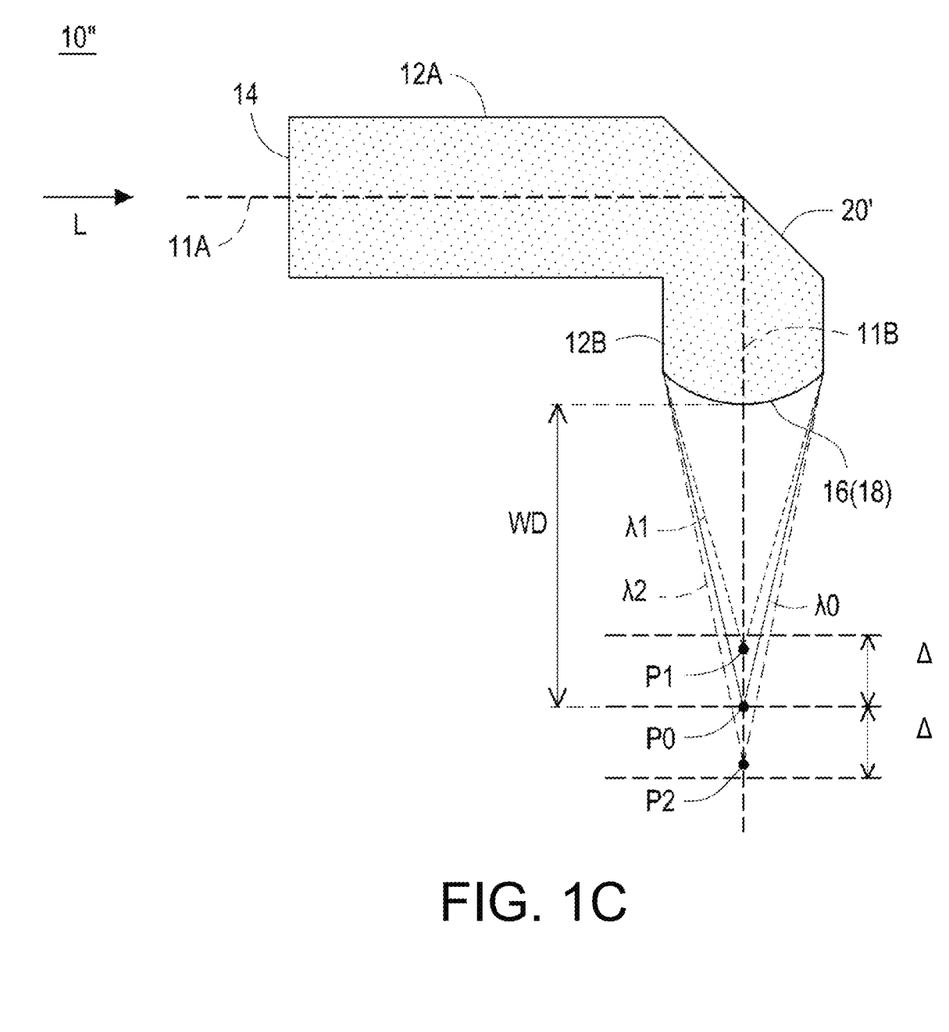
FIG. 1C is a schematic diagram of an optical probe according to still another embodiment of the disclosure.

FIG. 1C is a cross-sectional view of an optical probe 10" of another embodiment. The optical probe 10" includes two cylindrical lenses (i.e., a first cylindrical lens 12A and a second cylindrical lens 12B) and a reflector 20'. The reflector 20' is disposed between the first cylindrical lens 12A and the second cylindrical lens 12B to form an L-shaped appearance. The first cylindrical lens 12A, the second cylindrical lens 12B and the reflector 20' may be designed to be integrally formed to form a lens reflection structure. After the incident light L enters the first cylindrical lens 12A along a first optical axis 11A, it is reflected by the reflector 20' to pass through the second cylindrical lens 12B along a second optical axis 11B of the second cylindrical lens 12B, and is emitted through a light-emitting surface, i.e., the curved end surface 16 of the second cylindrical lens 12B. The first optical axis 11A of the first cylindrical lens 12A and the second optical axis 11B of the second cylindrical lens 12B are perpendicular to each other.

When the incident light L with different wavelengths $\lambda 0$, $\lambda 1$, and $\lambda 2$ is incident along the first optical axis of the first cylindrical lens 12A, it is reflected by the reflector 20' to enter the second cylindrical lens 12B, and is respectively converged to the working positions P0, P1, and P2. By setting the reflector 20', the optical probe 10" may be deflected by 90 degrees at the light-emitting surface, i.e., the curved end surface 16 (and the diffractive microstructure 18) of the second cylindrical lens 12B with respect to the first optical axis 11A of the first cylindrical lens 12A, so as to facilitate detections in different directions in use and increase operational flexibility.

According to the above embodiment, in both of FIG. 1B and FIG. 1C, the direction of the incident light L may be changed through the reflector 20 and the reflector 20'. In the optical probe 10' of FIG. 1B, the reflector 20 is located outside the cylindrical lens 12, so that the direction of the incident light L is changed by the reflector 20 after the incident light L leaves the cylindrical lens 12. In the optical probe 10" of FIG. 1C, the reflector 20' is located between the first cylindrical lens 12A and the second cylindrical lens 12B, and the three components are the integrally formed lens reflection structure, so that the incident light L changes the direction in the lens reflection structure before being emitted from the light-emitting surface of the lens reflection structure.

Referring to FIG. 1A, FIG. 1B and FIG. 1C, when the incident light L with different wavelengths λ0, λ1, and λ2 enters in a direction parallel to the first optical axis 11 (or 11A) of the cylindrical lens 12 (or the first cylindrical lens 12A), and leaves the cylindrical lens 12 (or the second cylindrical lens 12B) through the curved end surface 16, a part of the incident light L produces a diffraction effect through the diffractive microstructure 18 on the curved end surface 16 and is respectively converged at the working positions P0 and P1 where the diffraction order m=1. A part of the incident light L does not produce the diffraction effect when passing through the diffractive microstructure 18 on the curved end surface 16, which is equivalent to the diffraction order m=0. The incident light L that does not produce the diffraction effect may be refracted by a curved surface of the curved end surface 16 (not shown), and is converged at the working position P2.

Figure 2A:
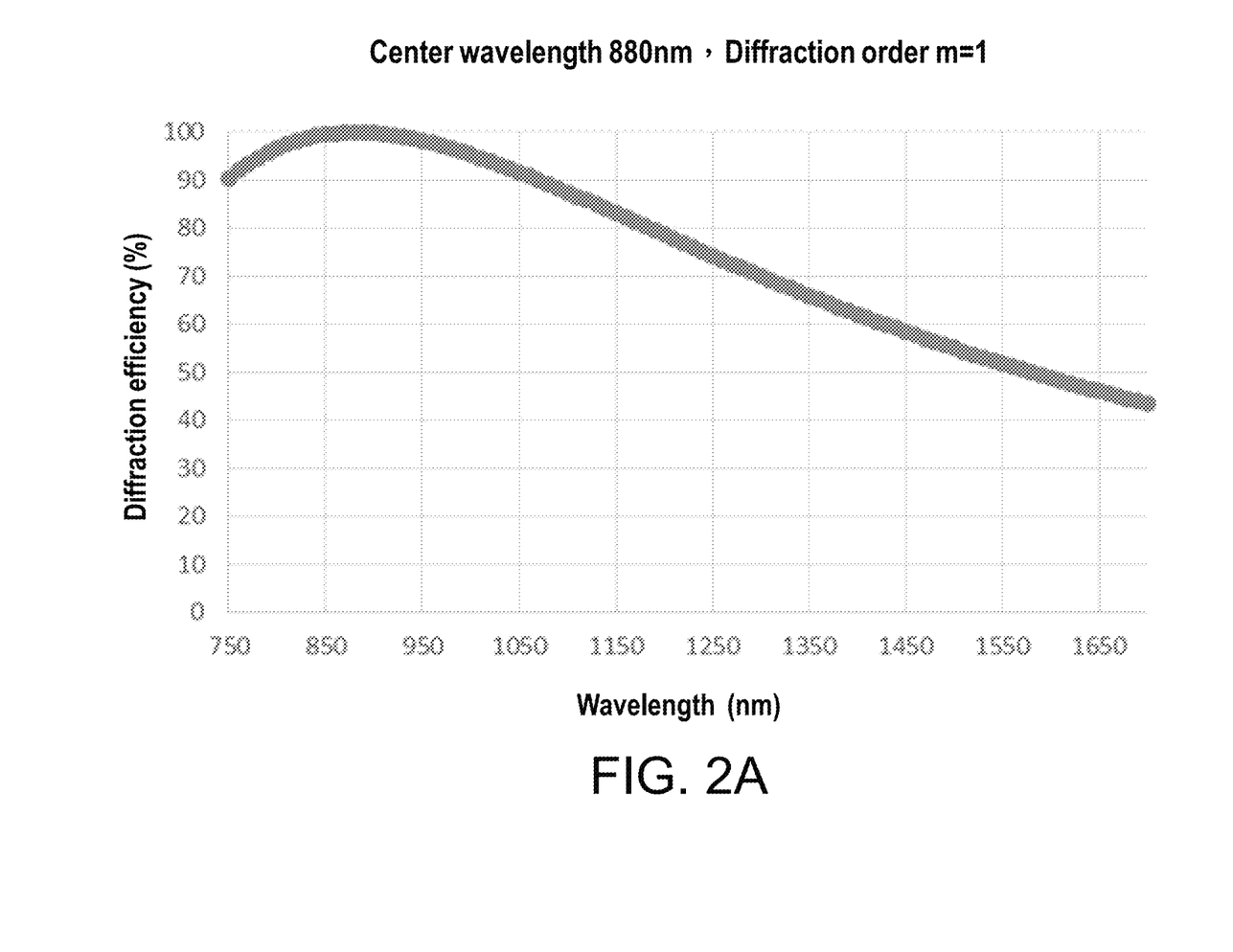
FIG. 2A is a schematic diagram of diffraction efficiency of a wavelength range according to an embodiment of the disclosure.
Figure 2B:
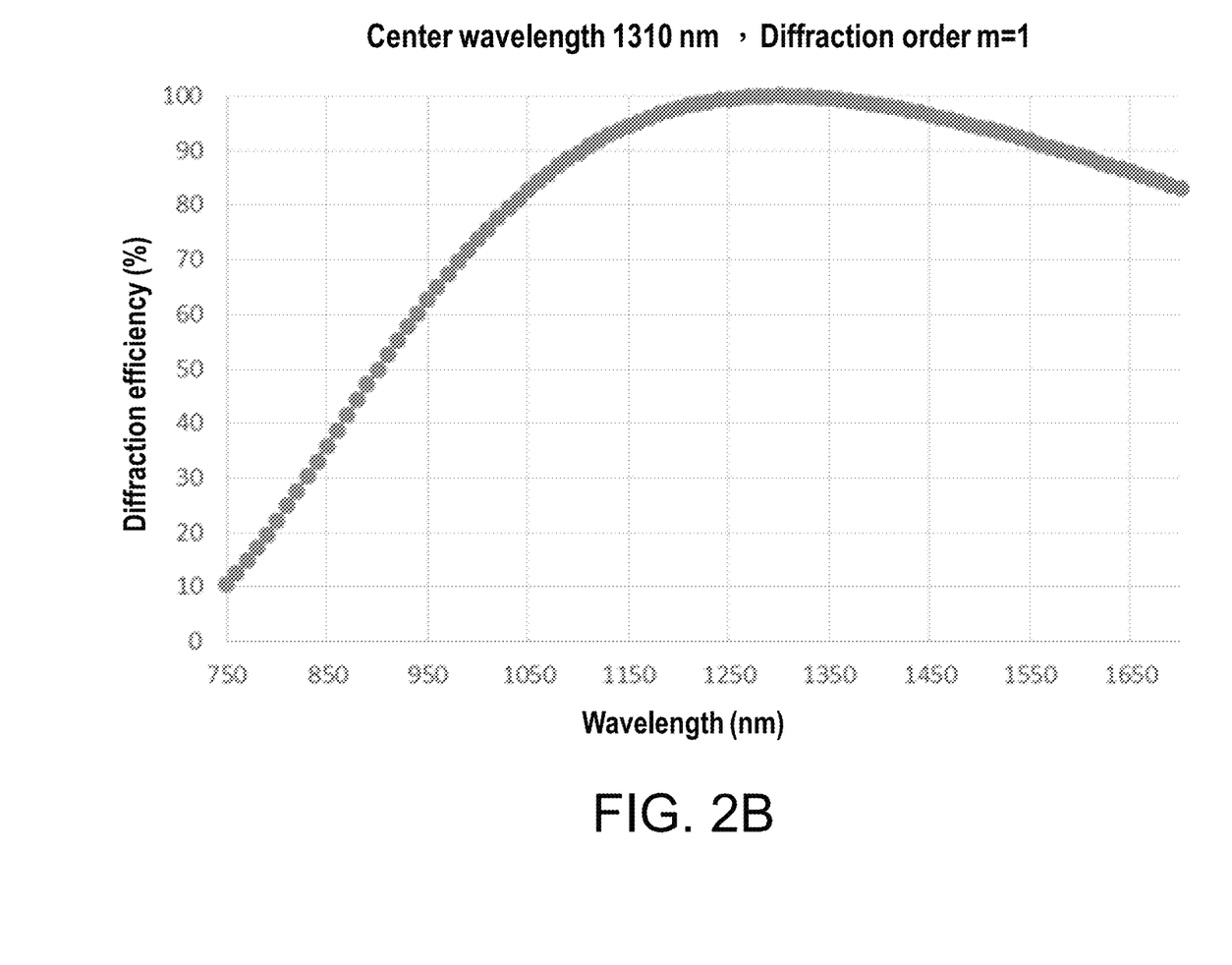
FIG. 2B is a schematic diagram of diffraction efficiency of another wavelength range according to an embodiment of the disclosure.

Referring to FIG. 2A and FIG. 2B, FIG. 2A and FIG. 2B respectively show diffraction efficiencies of the incident light L with the wavelength λ=750 nm to 1700 nm at the diffraction order m=1 under different design wavelengths.

The structure of the diffractive microstructure 18 is designed at the design wavelength λ0, so that when the wavelength of the incident light L is equal to the design wavelength λ0, it has good diffraction efficiency. The diffraction efficiency of the diffractive microstructure 18 is calculated according to a following equation (1):

$$E = 100\% \times \left\{ \frac{\sin\left[m\pi\left(\frac{\lambda 0}{\lambda} - 1\right)\right]}{m\pi\left(\frac{\lambda 0}{\lambda} - 1\right)} \right\}^2 \quad (1)$$

wherein E is the diffraction efficiency, λ0 is the design wavelength, λ is an optical coherent tomography light source wavelength (i.e., the incident light wavelength), and m is the diffraction order. According to equation (1), it is learned that under the given design wavelength λ0, different optical coherent tomography light source wavelengths have different diffraction efficiencies at the diffraction order m=1.

In an embodiment, FIG. 2A shows the diffraction efficiencies of the incident light with the wavelength λ=750 nm to 1700 nm at the diffraction order m=1 under the design wavelength λ0=880 nm.

As shown in FIG. 2A, the structure of the diffractive microstructure 18 is designed at the design wavelength λ0, and under the design wavelength λ0=880 nm, when the incident light wavelength λ=880 nm, the diffraction efficiency is the highest, which is 100%. When the incident light wavelength λ is gradually shortened from 880 nm to 750 nm, the diffraction efficiency is decreased along with the shortening of the wavelength, and the diffraction efficiency at this moment is about 90%. When the incident light wavelength λ is gradually increased from 880 nm to 1700 nm, the diffraction efficiency is decreased along with increase of the wavelength. When the incident light wavelength λ=1200 nm, the diffraction efficiency is about 80%. When the incident light wavelength λ=1200 nm to 1700 nm, the diffraction efficiency is less than 80%. At this time, the optical coherent tomography probe cannot read a signal of the corresponding incident light wavelength λ due to that the energy of the diffraction signal of the incident light wavelength λ is too low.

In addition, the deviations of the working position of the incident light wavelength λ=750 nm to 1700 nm at the diffraction order m=1 and the working position of the design wavelength λ0=880 nm at the diffraction order m=1 are all less than 10 nm. Namely, if the diffraction effect produced by the diffractive microstructure 18 alone is considered, when the design wavelength λ0=880 nm and the incident light wavelength λ=750 nm to 1700 nm, a deviation of the working position of the incident light at the diffraction order m=1 relative to the working position of the design wavelength λ0=880 nm at the diffraction order m=1 is less than 10 μm, which meets the working requirements of the optical coherent tomography probe.

In the embodiment, since the design wavelength λ0 belongs to a shorter wavelength, and the structure of the diffractive microstructure 18 is designed at the design wavelength λ0, it has a higher diffraction efficiency (greater than 80%) at a short wavelength, i.e., when the incident light wavelength λ=750 nm to 1185 nm. At long wavelengths, i.e., when the incident light wavelength λ=1185 nm to 1700 nm, the diffractive microstructure 18 has a lower diffraction efficiency (less than 80%).

In another embodiment, FIG. 2B shows diffraction efficiencies of the incident light wavelength λ=750 nm to 1700 nm at the diffraction order m=1 when the structure of the diffractive microstructure 18 is designed at the design wavelength λ0, and the design wavelength λ0=1310 nm.

As shown in FIG. 2B, when the design wavelength λ0=1310 nm and the incident light wavelength λ=1310 nm, the diffraction efficiency is the highest, which is 100%. When the incident light wavelength λ is gradually increased from 1310 nm to 1700 nm, the diffraction efficiency is decreased along with increase of the incident light wavelength λ, and the diffraction efficiency at this moment is about 83%. When the incident light wavelength λ is gradually decreased from 1310 nm to 750 nm, the diffraction efficiency is decreased along with shortening of the wavelength. When the incident light wavelength λ=1045 nm, the diffraction efficiency is about 80%. When the incident light wavelength λ=750 nm to 1045 nm, the diffraction efficiency is less than 80%. At this time, the optical coherent tomography probe is unable to read the signal of the corresponding incident light wavelength λ due to that the energy of the diffraction signal of the incident light wavelength λ is too low.

In addition, the deviations of the working position of the incident light wavelength λ=750 nm to 1700 nm at the diffraction order m=1 and the working position of the design wavelength λ0=1310 nm at the diffraction order m=1 are all less than 10 nm. Namely, if the diffraction effect produced by the diffractive microstructure 18 alone is considered, when the design wavelength λ0=1310 nm and the incident light wavelength λ=750 nm to 1700 nm, a deviation of the working position of the incident light at the diffraction order m=1 relative to the working position of the design wavelength λ0=1310 nm at the diffraction order m=1 is less than 10 μm, which meets the working requirements of the optical coherent tomography probe.

In the embodiment, since the design wavelength λ0 belongs to a longer wavelength, and the structure of the diffractive microstructure 18 is designed at the design wavelength λ0, it has a higher diffraction efficiency (greater than 80%) at a long wavelength, i.e., when the incident light wavelength λ=1045 nm to 1700 nm. At short wavelengths, i.e., when the incident light wavelength λ=750 nm to 1045 nm, the diffractive microstructure 18 has a lower diffraction efficiency (less than 80%).

Therefore, from FIG. 2A (the design wavelength λ0=880 nm) and FIG. 2B (the design wavelength λ0=1310 nm), it is learned that when the incident light wavelength λ=750 nm to 1700 nm, the diffraction efficiencies of some wavelength ranges may be higher (i.e., when the design wavelength λ0=880 nm, the diffraction efficiency of the incident light wavelength λ=750 nm to 1185 nm is higher, and when the design wavelength λ0=1310 nm, the diffraction efficiency of the incident light wavelength λ=1045 nm to 1700 nm is higher), and the diffraction efficiencies of some wavelength ranges is lower (i.e., when the design wavelength λ0=880 nm, the diffraction efficiency of the incident light wavelength λ=1185 nm to 1700 nm is lower, and when the design wavelength λ0=1310 nm, the diffraction efficiency of the incident light wavelength λ=750 nm to 1045 nm is lower).

The diffractive microstructure 18 is designed for the wavelength range with high diffraction efficiency. Referring to FIG. 1A, the diffractive microstructure 18 is a concentric ring-shaped structure relative to the first optical axis 11, and takes the first optical axis 11 as a circle center. Regarding the design of the diffractive microstructure 18, a following equation (2) is used to simulate a phase profile φ of the incident light, and the phase profile φ is used as an approximation of a profile of the diffractive microstructure 18 in a surface depth stepwise manner, wherein the equation (2) is:

$$\phi = \Sigma_{n=1}^{10} C_n R^{2n} \quad (2)$$

wherein Cn is a phase coefficient, and R is a radius of the diffractive microstructure 18.

Based on the phase profile φ and the range of the design wavelength λ0, a light diffraction direction of the diffractive microstructure 18 may be calculated, and the diffraction efficiency and chromatic dispersion of the diffractive microstructure 18 may be calculated.

A height h of the diffractive microstructure 18 is derived from a following equation (3):

$$h = \frac{\lambda 0}{n0 - 1} \quad (3)$$

wherein h is the height of the diffractive microstructure, λ0 is the design wavelength, and n0 is a material refractive index of the diffractive microstructure.

In order to increase the energy of the wavelength range with lower diffraction efficiency at its working position (a position of the wavelength range at the diffraction order m=1), a shape of the curved end surface 16 of the cylindrical lens is designed, so that a part of the incident light L of the wavelength range with lower diffraction efficiency at the diffraction order m=0, i.e. the incident light L that does not produce the diffraction effect, may be refracted by the curved end surface 16 to make the incident light L to be converged at the working position corresponding to the diffraction order m=1 of the wavelength range, so as to strengthen the energy of the wavelength range at the working position.

When the diffraction order m=0, the diffractive microstructure 18 does not produce a diffraction effect on the incident light L. At this time, the diffractive microstructure 18 is equivalent to not existing for the incident light L with the diffraction order m=0. Therefore, for the incident light L with the diffraction order m=0, the effect of the diffractive microstructure 18 may not be considered.

When the curved end surface 16 is aspherical, the shape of the curved end surface 16 may be designed according to a following equation (4), so that the incident light L of the wavelength range with low diffraction efficiency may be refracted and converged at the working position P0, wherein the working distance WD is a distance from the curved end surface 16 to the working position P0, and the equation (4) is an aspheric surface profile equation:

$$H = \frac{cR^2}{1 + \sqrt{1 - (1+k)c^2 R}} + AR^4 + BR^6 + CR^8 \quad (4)$$

wherein H is a height of a surface parallel to the optical axis (i.e., a height of the curved end surface 16), R is a radius of the curved end surface 16, c is a curvature of the curved end surface 16, k is a conic constant, and A, B, and C are non-spherical constants.

It should be noted that in the equation (2), R is the radius of the diffractive microstructure 18, and in the equation (4), R is the radius of the curved end surface 16. In an actual design, the radius R of the diffractive microstructure 18 may be designed to be equal to the radius R of the curved end surface 16, so that the same reference numeral is used here for representation. The radius R of the curved end surface 16 and the same radius R of the diffractive microstructure 18 may have the respective corresponding curved surface height H and diffractive microstructure height h, and the height and the order are required to be added to form the effects of refraction and diffraction.

Two embodiments are provided below to illustrate how to design the curved end surface 16 and the diffractive microstructure 18 corresponding to a specific design wavelength λ0.

Embodiment 1

Referring to FIG. 1A, the design wavelength is λ0=880 nm. The incident light wavelength λ=750 nm to 1700 nm. In detail, the incident light L includes incident light with a first wavelength λ1=750 nm to 1250 nm and incident light with a second wavelength λ2=1200 nm to 1700 nm. The working position P0 is a position where the diffraction order m=1 when the design wavelength λ0=880 nm. The working distance WD is a distance between the working position P0 and the curved end surface 16. According to a diffraction efficiency distribution of FIG. 2A, the curved end surface 16 and the diffractive microstructure 18 of the cylindrical lens 12 are designed, wherein (1) the diffractive microstructure 18 is designed as that when the incident light L with the first wavelength λ1=750 nm to 1250 nm passes through the curved end surface 16 of the cylindrical lens 12, the incident light L produces the diffraction effect with the diffractive microstructure 18 and is converged to a first wavelength working position P1, i.e., a position where the diffraction order m=1, which has a deviation from the working position P0 of the design wavelength λ0 (i.e., the working position of the optical probe 10) less than 10 μm; (2) the curved end surface 16 of the cylindrical lens 12 is designed so that the part of the incident light L with the second wavelength λ2=1200 nm to 1700 nm at the diffraction order m=0 is refracted and converged to the second wavelength working position P2 through the curved end surface 16 of the cylindrical lens 12, which has a deviation from the working position P0 of the design wavelength λ0 less than 10 μm.

Figure 3A:
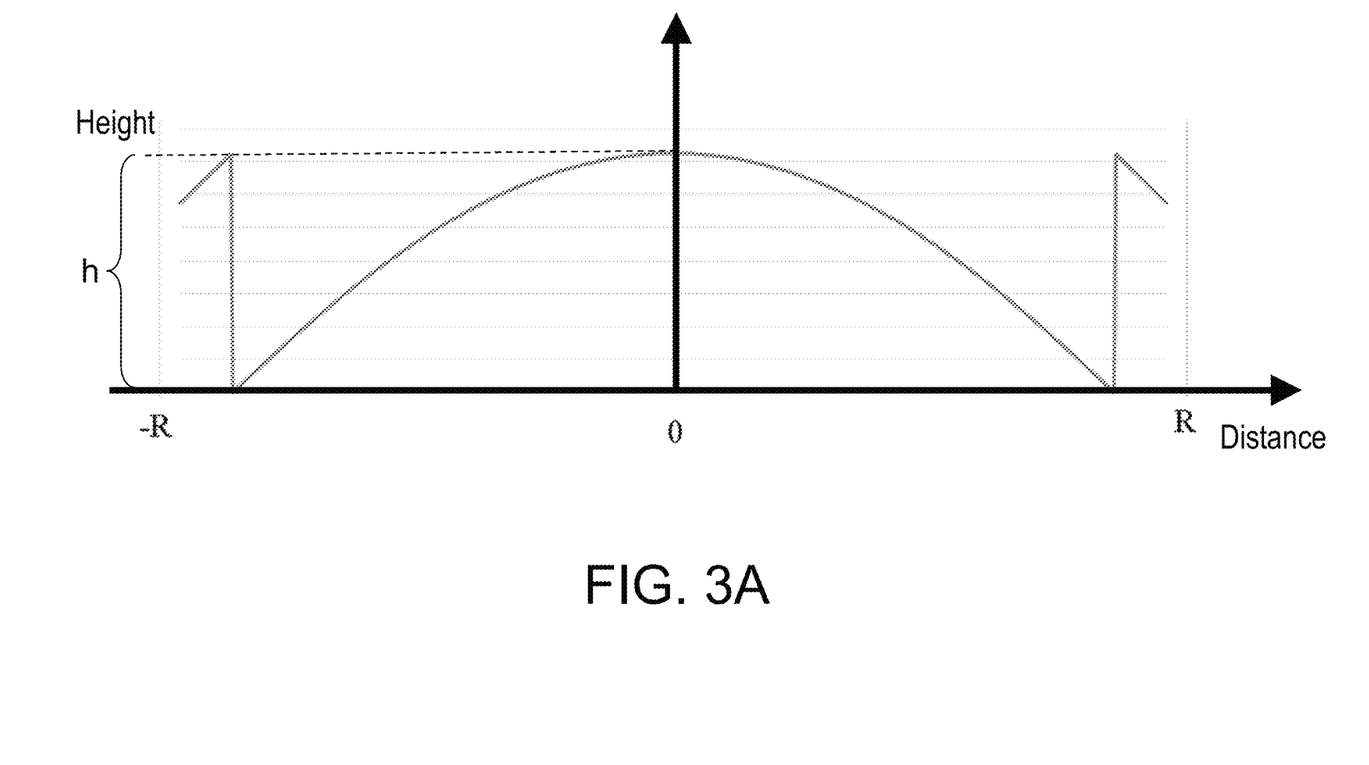
FIG. 3A is a cross-sectional view of a diffractive microstructure according to an embodiment of the disclosure.

When the design wavelength λ0=880 nm, the structure of the diffractive microstructure 18 is as shown in FIG. 3A. When the incident light L of the design wavelength λ0 and the first wavelength λ1 satisfies 0.63<λ0/λ1<1.25, the diffraction efficiency of the incident light L is greater than 80%. At this time, the incident light L having the first wavelength $\lambda_1$ within such range has sufficiently high diffraction efficiency, so that the system may measure a signal of the first wavelength $\lambda_1$ at the first wavelength working position P1 through the diffraction effect. Conversely, when the wavelength of the incident light L is outside the above range, the diffraction efficiency of the incident light L is less than 80%, and the system cannot measure the signal of the incident light L at the working position corresponding to the wavelength of the incident light L through the diffraction effect.

According to the equation (2), in parameters of the phase profile $\varphi$ of the diffractive microstructure 18, a phase coefficient $C_1$ needs to satisfy $C_1>0.011$, so that the incident light L of the first wavelength $\lambda_1$=750 nm to 1250 nm may produce the diffraction effect. In an embodiment, the first two phase coefficients $C_1$ and $C_2$ are respectively $C_1$=1.10000E-02 and $C_2$=-1.37564E-02.

Moreover, the diffractive microstructure 18 needs to satisfy the following condition. A focal length f2 of the diffractive microstructure 18 needs to satisfy f2>-50 mm, so as to produce the diffraction effect on the incident light L of the first wavelength $\lambda_1$=750 nm to 1250 nm, and a deviation of the first wavelength working position P1 from the working position P0 of the design wavelength $\lambda_0$ is less than 10 μm. The height h of the diffractive microstructure 18 needs to satisfy 1.29 μm<h<1.75 μm, so as to produce the diffraction effect on the incident light L of the first wavelength $\lambda_1$=750 nm to 1250 nm.

Figure 3B:
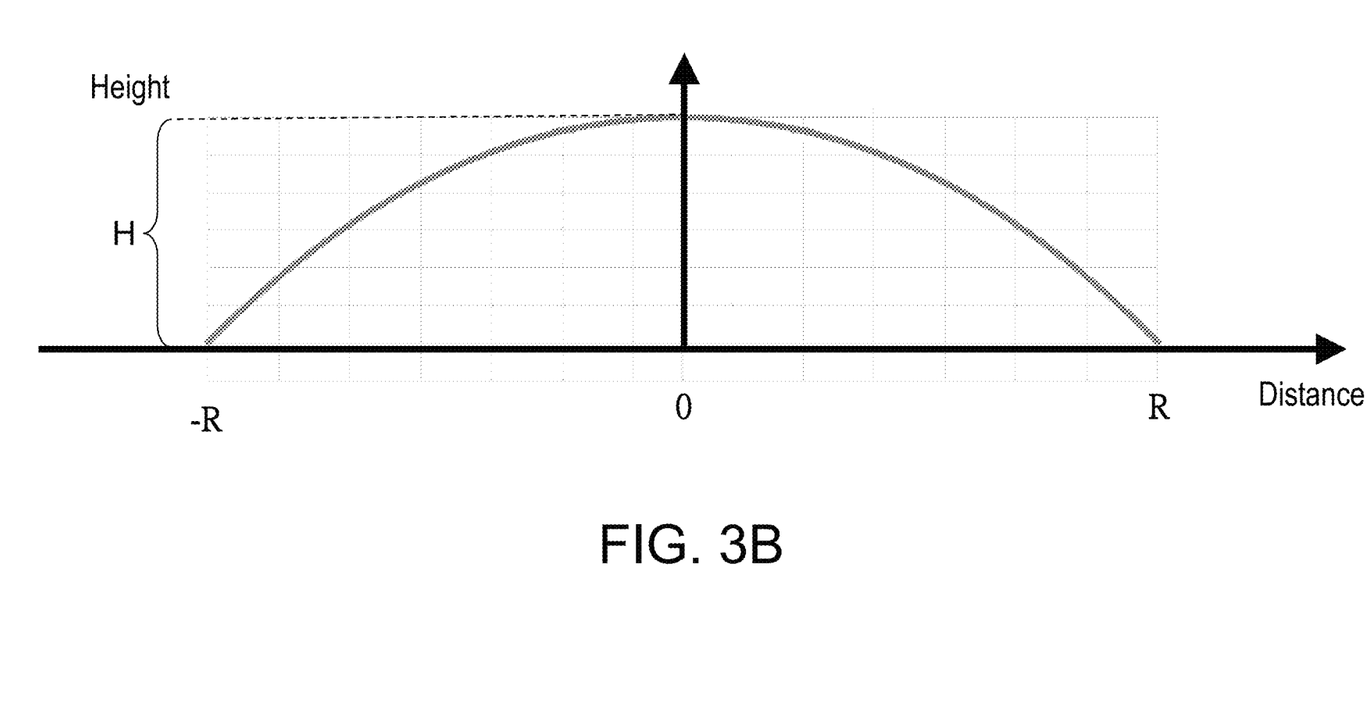
FIG. 3B is a cross-sectional view of a curved end surface of a cylindrical lens according to an embodiment of the disclosure.

Referring to FIG. 1A and FIG. 3B, when the design wavelength $\lambda_0$=880 nm, the curved end surface 16 is aspheric, and the shape of the curved end surface 16 is determined by the equation (4), so that the incident light L with the second wavelength $\lambda_2$=1200 nm to 1700 nm is refracted by the curved end surface 16 and converged at the second wavelength working position P2. In an embodiment, the shape of the curved end surface 16 is determined according to the equation (4), and some of the parameters are: a curvature c of the curved end surface 16 is -1.9953 (i.e., c=-1.9953), a conic constant k=-0.398145, and an aspheric constant A=1.38111.

In an embodiment, a focal length f1 of the curved end surface 16 needs to satisfy f1>0.8 mm, so that the incident light L with the second wavelength $\lambda_2$=1200 nm to 1700 nm may be refracted by the curved end surface 16 and converged at the second wavelength working position P2, which has a deviation from the working position P0 of the design wavelength $\lambda_0$ less than 10 μm. The height H of the curved end surface 16 needs to satisfy 0.06 mm<H<0.2 mm, so as to produce a refraction effect on the incident light L with the second wavelength $\lambda_2$=1200 nm to 1700 nm.

In addition, a total focal length f of the optical probe 10, the focal length f1 of the curved end surface 16 and the focal length f2 of the diffractive microstructure 18 are required to satisfy a following condition: f/f1>1.1, wherein the total focal length f of the optical probe 10 is a total focal length obtained after combination of the curved end surface 16 of the cylindrical lens 12 and the diffractive microstructure 18, so as to ensure a ratio configuration of the refraction effect and the diffraction effect.

According to the above design, the maximum deviation of the working positions (P1, P2) of the incident light L of the incident light wavelength $\lambda$=750 nm to 1700 nm relative to the working position P0 of the design wavelength $\lambda_0$=880 nm is about 9.5 μm, which is in line with a requirement of a practical application that the deviation of the working position is less than 10 μm. Therefore, the working positions (P1, P2) of the incident light L with the incident light wavelength $\lambda$=750 nm to 1700 nm are approximately the same as the working position P0 of the design wavelength $\lambda_0$=880 nm.

Embodiment 2

Referring to FIG. 1A, the design wavelength $\lambda_0$=1310. The wavelength range of the incident light is $\lambda$=750 nm to 1700 nm. In detail, the incident light L includes incident light of the first wavelength $\lambda_1$=950 nm to 1700 nm and incident light of the second wavelength $\lambda_2$=750 nm to 950 nm. The working position P0 is a position where the diffraction order m=1 when the design wavelength $\lambda_0$=1310 nm. The working distance WD is a distance between the working position P0 and the curved end surface 16. According to a diffraction efficiency distribution of FIG. 2B, the curved end surface 16 and the diffractive microstructure 18 of the cylindrical lens 12 are designed, wherein (1) the diffractive microstructure 18 is designed as that when the incident light L with the first wavelength $\lambda_1$=950 nm to 1700 nm passes through the curved end surface 16 of the cylindrical lens 12, the incident light L produces the diffraction effect with the diffractive microstructure 18 and is converged to a first wavelength working position P1, i.e., a position where the diffraction order m=1, which has a deviation from the working position P0 of the design wavelength $\lambda_0$ (i.e., the working position of the optical probe 10) less than 10 μm; (2) the curved end surface 16 of the cylindrical lens 12 is designed so that the part of the incident light L with the second wavelength $\lambda_2$=750 nm to 950 nm at the diffraction order m=0 is refracted and converged to the second wavelength working position P2 through the curved end surface 16 of the cylindrical lens 12, which has a deviation from the working position P0 of the design wavelength $\lambda_0$ less than 10 μm.

Figure 4A:
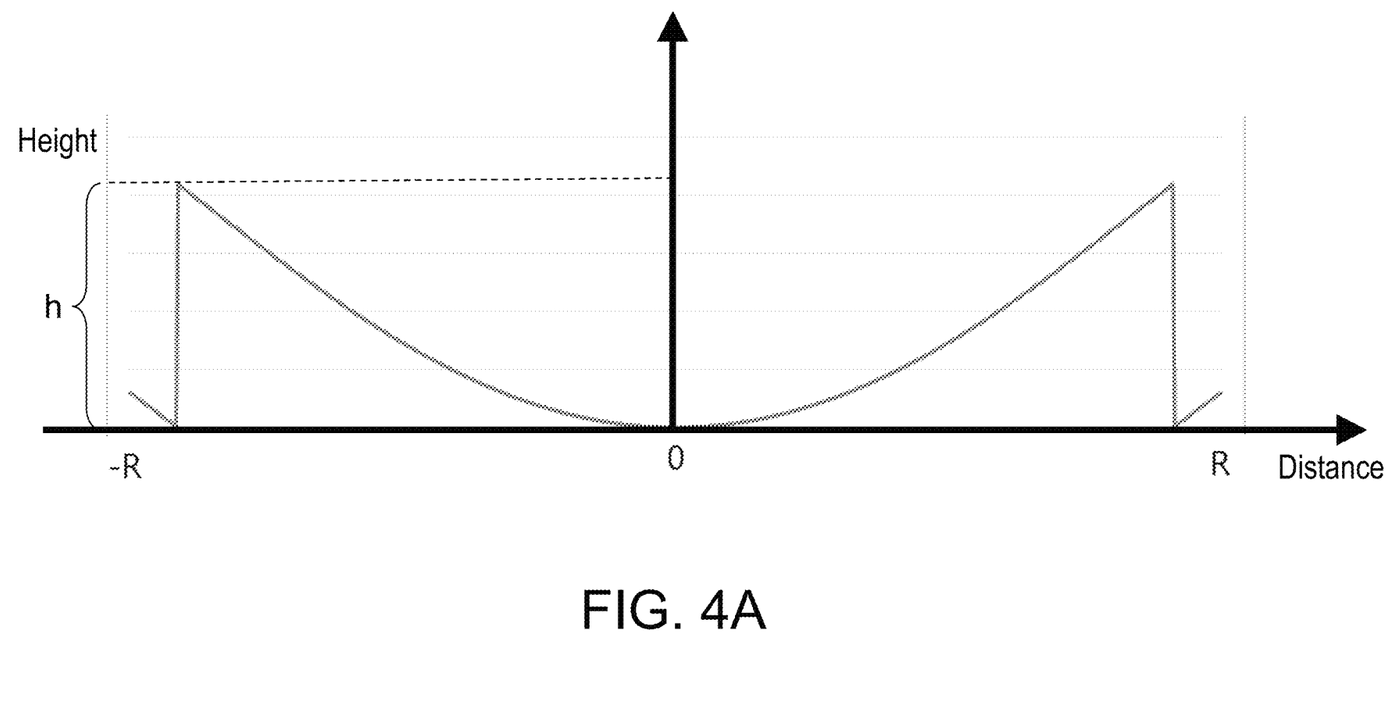
FIG. 4A is a cross-sectional view of another diffractive microstructure according to an embodiment of the disclosure.

When the design wavelength $\lambda_0$=1310 nm, the structure of the diffractive microstructure 18 is as shown in FIG. 4A. When the incident light L of the design wavelength $\lambda_0$ and the first wavelength $\lambda_1$ satisfies 0.7<$\lambda_0/\lambda_1$<1.68, the diffraction efficiency of the incident light L is greater than 80%. At this time, the incident light L having the first wavelength $\lambda_1$ within such range has sufficiently high diffraction efficiency, so that the system may measure a signal of the first wavelength $\lambda_1$ at the first wavelength working position P1 through the diffraction effect. Conversely, when the wavelength of the incident light L is outside the above range, the diffraction efficiency of the incident light L is less than 80%, and the system cannot measure the signal of the incident light L at the working position corresponding to the wavelength of the incident light L through the diffraction effect.

According to the equation (2), in the parameters of the phase profile $\varphi$ of the diffractive microstructure 18, a phase coefficient $C_1$ needs to satisfy $C_1$<-0.01, so that the incident light L of the first wavelength $\lambda_1$=950 nm to 1700 nm may produce the diffraction effect. In an embodiment, the first two phase coefficients $C_1$ and $C_2$ are respectively $C_1$=-1.00000E-02 and $C_2$=8.68449E-03.

In addition, the diffractive microstructure 18 needs to satisfy the following condition. The focal length f2 of the diffractive microstructure 18 needs to satisfy f2<50 mm, so as to produce the diffraction effect on the incident light L of the first wavelength $\lambda_1$=950 nm to 1700 nm, and a deviation of the first wavelength working position P1 from the working position P0 of the design wavelength $\lambda_0$ is less than 10 μm. The height h of the diffractive microstructure 18 needs to satisfy 1.93 μm<h<3.15 μm, so as to produce the diffraction effect on the incident light L of the first wavelength λ1=950 nm to 1700 nm.

Figure 4B:
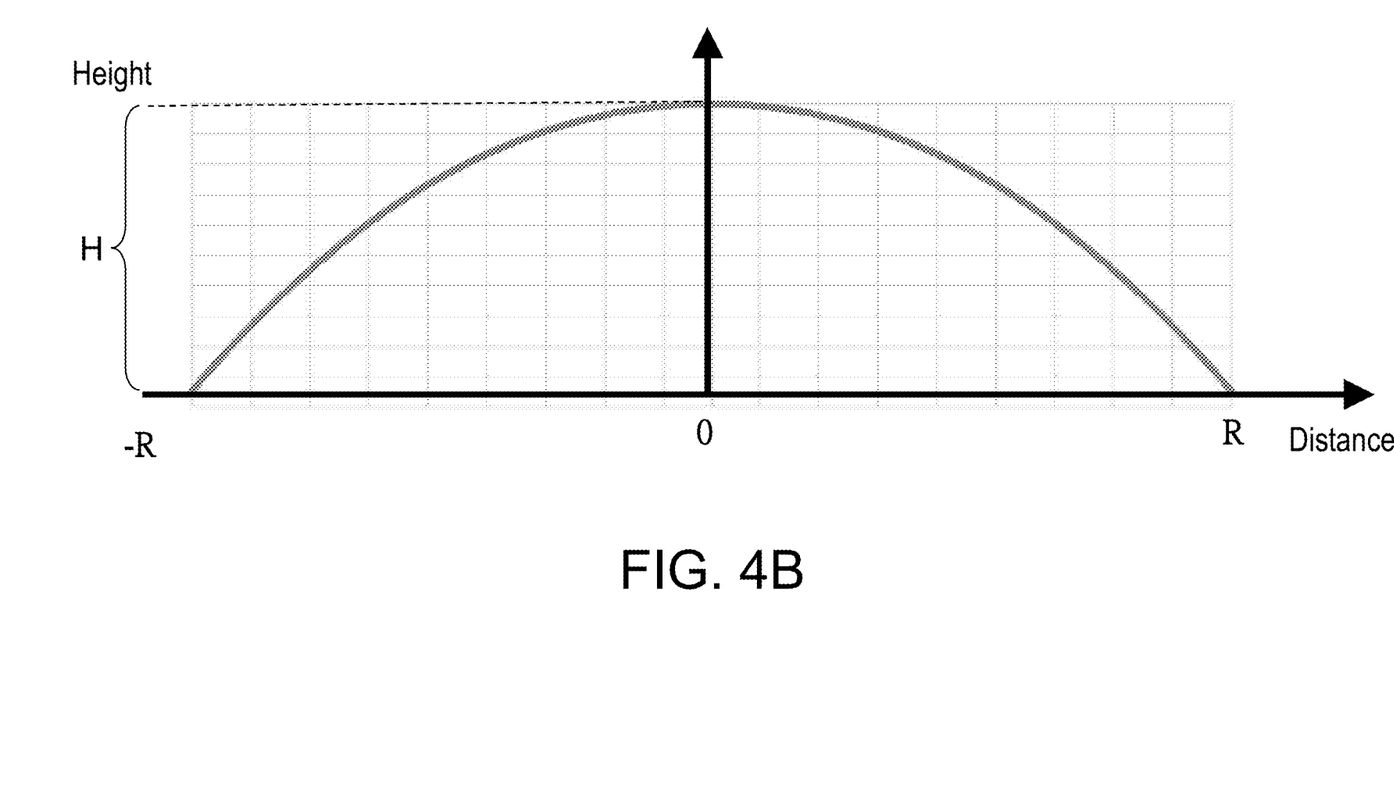
FIG. 4B is a cross-sectional view of another curved end surface of a cylindrical lens according to an embodiment of the disclosure.

Referring to FIG. 1A and FIG. 4B, when the design wavelength λ0=1310 nm, the curved end surface 16 is aspheric, and the shape of the curved end surface 16 is determined by the equation (4), so that the incident light L with the second wavelength λ2=750 nm to 950 nm is refracted by the curved end surface 16 and converged at the second wavelength working position P2. In an embodiment, the shape of the curved end surface 16 is determined according to the equation (4), and some of the parameters are: a curvature c of the curved end surface 16 is −1.8 (i.e., c=−1.8), a conic constant k=−0.423182, and an aspheric constant A=1.03886.

In an embodiment, the focal length f1 of the curved end surface 16 needs to satisfy f1<0.8853 mm, so that the incident light L with the second wavelength λ2=750 nm to 950 nm may be refracted by the curved end surface 16 and converged at the second wavelength working position P2, which has a deviation from the working position P0 of the design wavelength λ0 less than 10 μm. The height H of the curved end surface 16 needs to satisfy 0.06 mm<H<0.2 mm, so as to produce a refraction effect on the incident light L with the second wavelength λ2=750 nm to 950 nm.

In addition, a total focal length f of the optical probe 10, the focal length f1 of the curved end surface 16 and the focal length f2 of the diffractive microstructure 18 are required to satisfy a following condition: f/f1<0.982, wherein the total focal length f of the optical probe 10 is a total focal length of the curved end surface 16 of the cylindrical lens 12 and the diffractive microstructure 18 after combination, so as to ensure a ratio configuration of the refraction effect and the diffraction effect.

According to the above design, the maximum deviation of the working positions (P1, P2) of the incident light L of the incident light wavelength λ=750 nm to 1700 nm relative to the working position P0 of the design wavelength λ0=1310 nm is about 7.6 μm, which is in line with a requirement of a practical application that the deviation of the working position is less than 10 μm. Therefore, the working positions (P1, P2) of the incident light L with the incident light wavelength λ=750 nm to 1700 nm are approximately the same as the working position P0 of the design wavelength λ0=880 nm.

The optical coherent tomography probe of the disclosure combines a light-emitting end surface of the cylindrical lens with a curved surface and a diffractive microstructure, so that the cylindrical lens has the diffraction effect and the refraction effect at the same time, and the working distances within the incident light wavelength range 750 to 1700 are approximately the same, which increases a usable wavelength range of the optical coherent tomography probe, and maintains the energy of the whole waveband to be greater than >80%.

According to an embodiment, the optical probe of the disclosure uses a cylindrical lens, and a light-emitting surface thereof is a combination of a curved surface and a diffractive microstructure, which may produce a diffraction effect and a refraction effect on the incident light of different wavelengths at the same time. In the wavelength range of high diffraction efficiency, the diffraction effect may be used for detection. In the wavelength range of low diffraction efficiency, the design of the curved surface in the cylindrical lens may be used to refract the incident light to enhance the light energy. The incident light with the wavelength range of 750 nm to 1700 nm may have approximately the same working distance, which expands the wavelength range of the optical coherent tomography probe, and at the same time achieves higher resolution, higher contrast, and deeper penetration depth.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An optical probe, comprising:
   a cylindrical lens, adapted to receive and transmit an incident light, wherein a light-emitting surface of the cylindrical lens is a curved end surface, and the curved end surface has a concentric ring-shaped diffractive microstructure; and
   a reflector, wherein the cylindrical lens comprises two cylindrical lenses, and the reflector is disposed between the cylindrical lenses to form an L-shaped appearance,
   wherein a working position of the optical probe is a position where a diffraction order is 1 when the incident light having a design wavelength passes through the diffractive microstructure;
   when the incident light having a first wavelength passes through the cylindrical lens, the incident light produces a diffraction effect with the diffractive microstructure and is converged at a first wavelength working position with the diffraction order of 1, and the first wavelength working position and the working position of the optical probe are approximately the same; and
   after the incident light having a second wavelength is refracted by the curved end surface of the cylindrical lens, the incident light is converged at a second wavelength working position, and the second wavelength working position is approximately the same as the working position of the optical probe,
   wherein the design wavelength is between the first wavelength and the second wavelength.

2. The optical probe as claimed in claim 1, wherein a deviation of the first wavelength working position from the working position of the optical probe is less than 10 μm, and a deviation of the second wavelength working position from the working position of the optical probe is less than 10 μm.

3. The optical probe as claimed in claim 1, wherein the first wavelength λ1 of the incident light is 750 nm to 1250 nm, and the second wavelength λ2 of the incident light is 1200 nm to 1700 nm.

4. The optical probe as claimed in claim 3, wherein the design wavelength λ0 of the diffractive microstructure and the first wavelength λ1 satisfy a following condition: 0.63<λ0/λ1<1.25, wherein diffraction efficiency of the incident light having the first wavelength is >80%.

5. The optical probe as claimed in claim 3, wherein a height h of the diffractive microstructure satisfies a following condition: 1.29 μm<h<1.75 μm.

6. The optical probe as claimed in claim 3, wherein a phase coefficient C1 of a phase profile of the diffractive microstructure satisfies a following condition: C1>0.011.

7. The optical probe as claimed in claim 3, wherein a focal length f2 of the diffractive microstructure satisfies a following condition: f2>−50 mm.

8. The optical probe as claimed in claim 3, wherein a focal length f1 of the curved end surface of the cylindrical lens satisfies a following condition: f1>0.8 mm.

9. The optical probe as claimed in claim 3, wherein a total focal length f of the optical probe and a focal length f1 of the curved end surface of the cylindrical lens satisfy a following condition: f/f1>1.1, wherein the total focal length f of the optical probe is a total focal length obtained after combination of the curved end surface of the cylindrical lens and the diffractive microstructure.

10. The optical probe as claimed in claim 1, wherein the first wavelength $\lambda 1$ of the incident light is 950 nm to 1700 nm, and the second wavelength $\lambda 2$ of the incident light is 750 nm to 950 nm.

11. The optical probe as claimed in claim 10, wherein the design wavelength $\lambda 0$ of the diffractive microstructure and the first wavelength $\lambda 1$ satisfy a following condition: $0.7<\lambda 0/\lambda 1<1.68$, wherein diffraction efficiency of the incident light having the first wavelength is >80%.

12. The optical probe as claimed in claim 10, wherein a height h of the diffractive microstructure satisfies a following condition: 1.93 μm<h<3.15 μm.

13. The optical probe as claimed in claim 10, wherein a phase coefficient C1 of a phase profile of the diffractive microstructure satisfies a following condition: C1<−0.01.

14. The optical probe as claimed in claim 10, wherein a focal length f2 of the diffractive microstructure satisfies a following condition: f2<50 mm.

15. The optical probe as claimed in claim 10, wherein a focal length f1 of the curved end surface of the cylindrical lens satisfies a following condition: f1<0.8853 mm.

16. The optical probe as claimed in claim 10, wherein a total focal length f of the optical probe and a focal length f1 of the curved end surface of the cylindrical lens satisfy a following condition: f/f1<0.982, wherein the total focal length f of the optical probe is a total focal length obtained after combination of the curved end surface of the cylindrical lens and the diffractive microstructure.

17. The optical probe as claimed in claim 1, wherein a height H of the curved end surface satisfies a following condition: 0.06 mm<H<0.2 mm.

18. The optical probe as claimed in claim 1, further comprising a second reflector disposed behind the curved end surface of the cylindrical lens, wherein the incident light is reflected and turned by the second reflector after leaving the cylindrical lens.

* * * * *